(12) United States Patent
Flatland et al.

(10) Patent No.: US 6,228,061 B1
(45) Date of Patent: May 8, 2001

(54) TROCAR SEAL SYSTEM HAVING DUAL SEALS

(75) Inventors: Marty Flatland; Larry M. Kwapis, both of Kalamazoo; John Klinger, Richland, all of MI (US)

(73) Assignee: Imagyn Medical Technologies California, Inc., Newport Beach, CA (US)

( * ) Notice: Subject to any disclaimer, the term of this patent is extended or adjusted under 35 U.S.C. 154(b) by 0 days.

(21) Appl. No.: 09/243,839

(22) Filed: Feb. 3, 1999

Related U.S. Application Data (60) Provisional application No. 60/073,522, filed on Feb. 3, 1998.

(51) Int. Cl.⁷ ................................................... A61M 5/178
(52) U.S. Cl. ..................................... 604/167.06; 604/264
(58) Field of Search ..................................... 604/167, 169, 604/256, 264; 606/185

(56) References Cited

U.S. PATENT DOCUMENTS

| | | | |
|---|---|---|---|
| 4,943,280 | * 7/1990 | Lander | 604/169 |
| 5,197,955 | * 3/1993 | Stephens et al. | 604/167 |
| 5,460,615 | * 10/1995 | Storz | 604/167 |
| 5,603,702 | * 2/1997 | Smith et al. | 604/256 |
| 5,807,338 | * 9/1998 | Smith et al. | 604/164 |

* cited by examiner

*Primary Examiner*—Sharon Kennedy
*Assistant Examiner*—Catherine Serke
(74) *Attorney, Agent, or Firm*—Howard & Howard (57) ABSTRACT

A trocar seal system is provided which permits surgical instruments of at least two different diameters to use the same cannula of a trocar while maintaining a sealed body cavity. The seal system mounts to a cannula of the trocar. The seal system includes an upper seal and a lower seal with the upper seal having a larger opening than the lower seal. The lower seal is mounted on a pivotal hinge plate which permits the lower seal to be moved out of the way when a larger diameter surgical instrument is inserted through the upper seal. When a smaller diameter surgical instrument is inserted through the upper seal, the lower seal is not moved out of its path and the lower seal seals about the smaller diameter surgical instrument.

2 Claims, 8 Drawing Sheets

TROCAR SEAL SYSTEM HAVING DUAL SEALS

This application claims the benefit of U.S. Provisional No. 60/073,522 filed Feb. 3, 1998.

BACKGROUND OF THE INVENTION

This invention relates generally to surgical instruments and, more particularly, to a trocar seal system. The trocar seal system of the present invention permits instruments of different sizes to be inserted into a trocar without breaking the gas seal created by the trocar. Unlike known trocar converters, the trocar seal system of the present invention is automatic and does not require any manipulation by the surgeon. The surgeon merely inserts the desired size of instrument and the trocar seal system provides the appropriate seal.

A trocar, in general, is a surgical instrument that can be used to create and maintain small hole-like incisions in a body cavity. These incisions are then used to introduce other surgical instruments into the body cavity to perform various surgical procedures. Conventional trocars include an obturator and a cannula. The obturator is a structure for penetrating a body wall to create the incision into the body cavity. The obturator can have either a sharp point or blunt tip. The cannula is a tube-like structure that is left in the incision made by the obturator to maintain the incision after the obturator is removed. Typically, the trocar comes as a unit that includes the obturator fitted inside of the cannula In surgical procedures involving trocars, the body cavity is generally inflated with carbon dioxide gas. Inflation of the body cavity with this gas creates a working "pocket" within the cavity and limits surgical instruments inserted through the cannula from puncturing internal organs. To maintain the cavity in an inflated state throughout the procedure, conventional cannulas include flaps and annular seals that prevent gas from escaping from the cavity when the obturator is withdrawn from the cannula and when other surgical instruments are subsequently inserted and withdrawn from the cannula. The flaps and annular seals are unable to prevent the escape of the gas if the diameter of the surgical instrument is less than the diameter of the hole in the annular seal. Thus, in a typical procedure a surgeon is limited in the size of instruments that can be inserted through a given cannula. Many times a surgeon wants to choose from a variety of surgical instruments having different diameters. With conventional trocars this requires that the surgeon either insert a number of cannulas each having a different size annular seal if he wishes to use surgical instruments with different diameters, or that the surgeon change the hole size by snapping one of several trocar converters, each having an annular seal with a different diameter hole, onto the cannula The latter option requires a collection of trocar converters and continuous changing of the trocar converters for various instrument sizes.

Therefore, it is desirable to provide a trocar that is capable of easily accommodating surgical instruments having different diameters while maintaining the inflated state of the body cavity.

SUMMARY OF THE INVENTION

The present invention overcomes the problems with traditional trocars by providing a trocar seal system, which has dual seals, that enables surgical instruments of different diameters to be inserted through the same trocar cannula. Each seal is configured to receive instruments of different diameters. One seal is for large instruments and the other for smaller instruments. When a large instrument is inserted, the smaller instrument seal moves out of the path of the instrument In the preferred embodiment, the smaller instrument seal is mounted to a platform or flapper door which pivots out of the path of the large instrument when it is inserted. When a small instrument is inserted, the platform remains stationary to receive the smaller instrument and the smaller instrument is sealed by the small seal.

In one embodiment of the present invention, the seal system includes a housing which is adapted to be mounted on one end of the cannula. In this embodiment, the housing preferably snaps onto the cannula. Mounted to the housing are a sleeve having a hole, a first instrument seal having a hole, and a platform or flapper door assembly. The sleeve has a first end and second end and the first instrument seal is mounted adjacent the first end of the sleeve. A hinge pin mounts the flapper door assembly adjacent the second end of the sleeve. The flapper door assembly includes a skid plate, second instrument seal and a hinge plate, each of which has a hole. The holes of the skid plate, second instrument seal and hinge plate are generally concentric. In one embodiment, the hole of the skid plate is eccentric with respect to the hole of the first instrument seal. In another embodiment, the hole of the skid plate is concentric with respect to the hole of the first instrument seal. The hinge plate is pivotally mounted to the sleeve and is movable between a normally closed position and an open position upon engagement by a larger diameter instrument In the normally closed position, a seal is maintained between the flapper door assembly and the second end of the sleeve. The hole of the second instrument seal has a smaller diameter than the hole in the first instrument seal. A duckbill valve is fitted into the bottom of the housing. The duckbill valve is a valve that is normally closed to prevent the escape of gas. The end of the valve has a slit that easily opens when an instrument is inserted through the valve. When an instrument is not present, gas pressure acts upon the angled end of the valve to keep it closed.

In a further embodiment of the present invention, the housing of the seal system is preferably threaded onto the end of the cannula. The housing has internal threads that mate with external threads on the cannula. Preferably, in this embodiment, the flapper door assembly is mounted to the housing as opposed to being mounted to the sleeve. The sleeve of this embodiment holds the first seal in the housing and holds a door seal in place. In the preferred embodiment, this sleeve is threaded into the housing for ease of assembly. In addition to the sleeve, a retainer ring is used to secure a duckbill valve to the housing. The duckbill valve of this embodiment is specially configured to fit into notches in the sleeve and has notches that receive tabs on the retainer ring.

DETAILED DESCRIPTION OF THE PREFERRED EMBODIMENT

Figure 1:
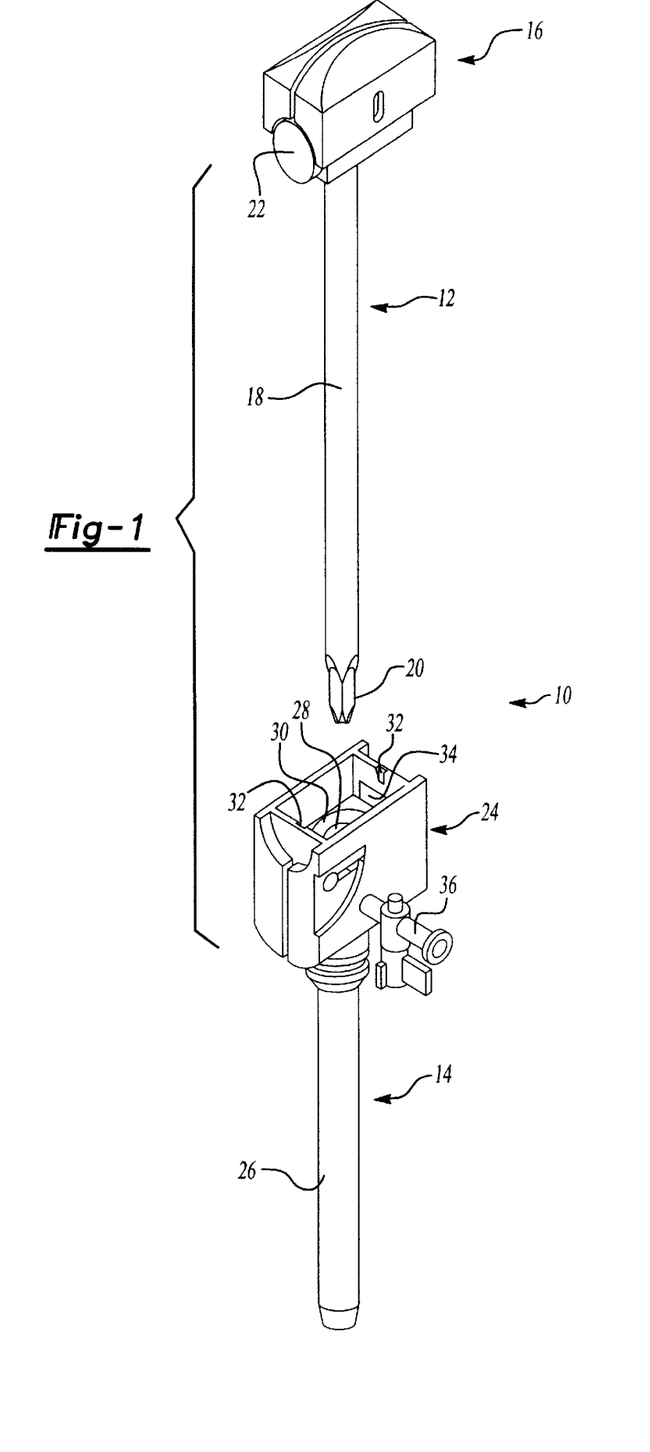
FIG. 1 is an exploded view of a conventional trocar.

Referring to the figures wherein like numerals indicate like or corresponding parts throughout the several views, in FIG. 1 a trocar is shown generally at 10. The trocar 10 includes an obturator 12 and a cannula 14. The design of the trocar 10 is identical to that disclosed in co-pending U.S. patent application Ser. No. 08/457,973, filed Jun. 1, 1995 and the disclosure in that application is hereby incorporated by reference.

The obturator 12 includes a handle 16 mounted on a shaft 18 having a cylindrical side wall and a sharp piercing tip 20. The handle 16 includes on opposing sides a pair of release buttons 22 to allow removal of the obturator 12 from the cannula 14 and, in particular, from handle 24. It should be understood by one of ordinary skill in the art that the piercing tip 20 may also have a blunt configuration (not shown) rather than the sharp configuration shown.

The cannula 14 includes handle 24 fixedly mounted on one end of an open ended tube 26. The handle 24 includes an opening 28 having an annular seal 30 which receives the shaft 18 and instruments. The handle 24 also includes an interior chamber, shown in phantom, one wall of which includes the opening 28. A flapper door, not shown, which is normally biased by a spring in a closed position, interacts with the annular seal 30 to automatically seal the opening 28. A valve 36 provides an opening into the interior chamber for the introduction of gas into the body cavity. The gas enters the valve 36 and flows through the tube 26. The opening 28 includes a pair of lead-in ramps 32 and a pair of notches 34 on opposing sides of the opening 28.

In use, the obturator 12 is releasably mounted into the cannula 14. A tabbed arm, not shown, on each of the buttons 22 engages the notches 34 as the shaft 18 of the obturator 12 is inserted into the open ended tube 26 of the cannula 14. When locked in position, the tip 20 of the obturator 12 extends beyond the distal end of the open ended tube 26 of the cannula 14. The diameter of the shaft 18 of the obturator 12 is selected so that the annular seal 30 provides an airtight seal around the shaft 18. The trocar 10 is then inserted through a wall of a body cavity making an incision. When the obturator 12 is withdrawn, the cannula 14 is left within the incision and the flapper door within the interior chamber maintains the inflated state of the body cavity.

Figure 2:
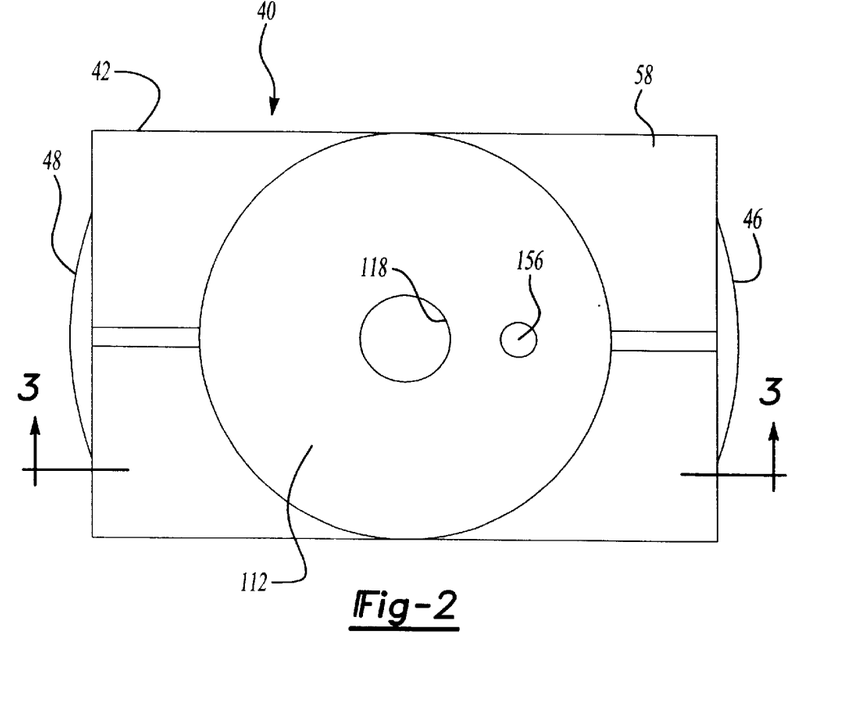
FIG. 2 is a top plan view of a trocar seal system designed according to this invention.
Figure 3:
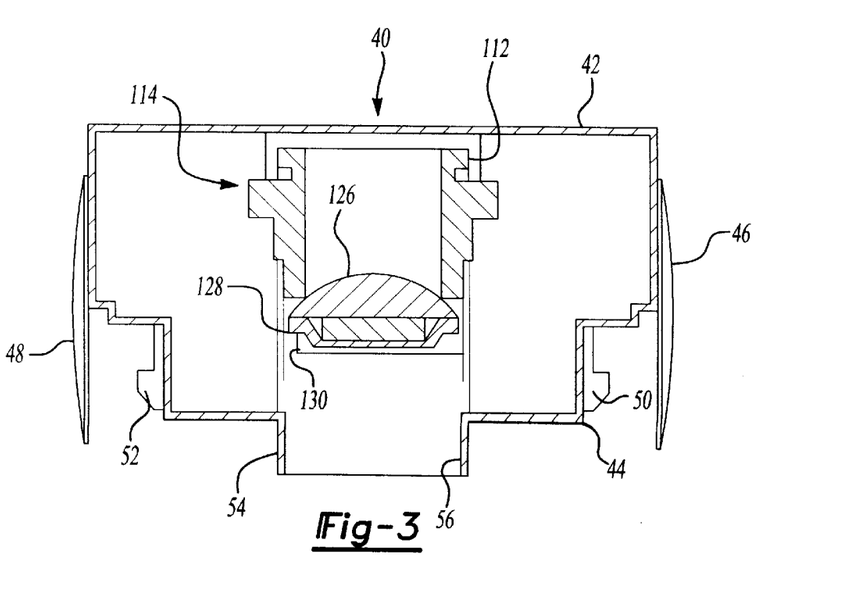
FIG. 3 is a cross-sectional side view along line 3—3 of a trocar seal system designed according to this invention.

In FIGS. 2 and 3, a top plan view and a cross-sectional side view of the trocar seal system of the present invention are shown generally at 40. It should be appreciated that the seal system 40 is adapted to be connected to handle 24. The trocar seal system 40 includes an upper housing 42 and a lower housing 44. Pivotally mounted on opposite sides of the upper housing 42 are release buttons 46 and 48. The release buttons 46 and 48 interact with a first tabbed arm 50 and a second tabbed arm 52, which together lock and permit release of the seal system 40 with respect to handle 24. The lower housing 44 further includes a projecting lip 54 having an opening 56. The upper housing 42 includes a top portion 58. An upper seal 112 and a sleeve 114 are mounted to the upper housing 42.

Figure 4:
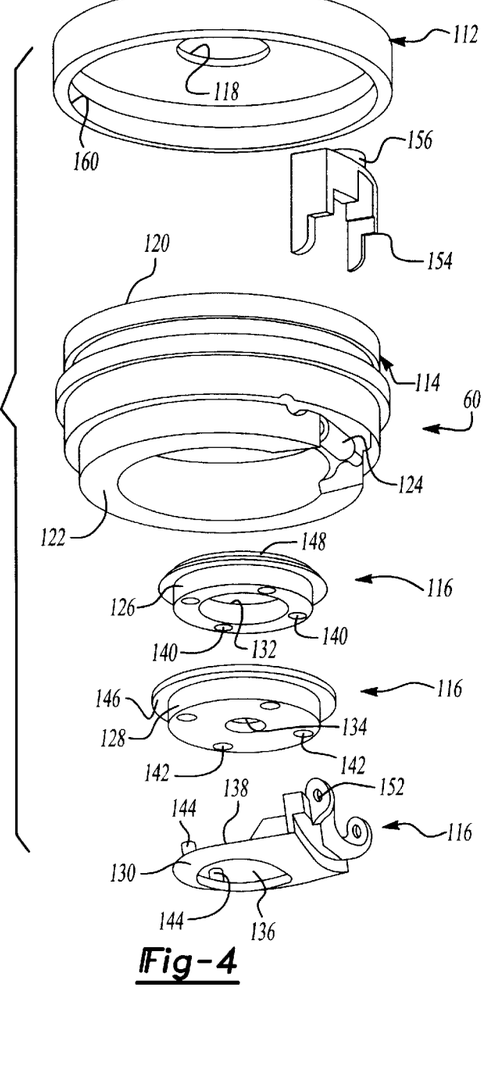
FIG. 4 is an exploded view of a portion of the interior of a trocar seal system designed according to this invention.

In FIG. 4, an exploded view of a portion of the interior assembly of the trocar seal system 40 is shown generally at 60. The interior assembly 60 as disclosed is a unit that can be mounted into the upper housing 42 by ultrasonic welding, gluing, etc. The interior assembly 60 includes the first instrument seal 112 which seals against a larger instrument, a sleeve 114, and flapper door assembly 116 which includes the second instrument seal 128 for smaller instruments. The sleeve 114 includes a first end 120 and a second end 122. A hinge pin 124 is mounted in the second end 122 of the sleeve 114 to mount the flapper door assembly 116 to the sleeve 114. The flapper door assembly 116 includes a skid plate 126, second instrument seal 128, and a hinge plate 130. The skid plate 126 has a hole 132, the second instrument seal 128 has a hole 134, and the hinge plate 130 has a hole 136 and a cup-shaped first side 138. The holes 132, 134 and 136 are sized to receive the smaller instruments. The skid plate 126 is curved slightly at 148 to aid in deflecting the flapper door 116 as a larger instrument is inserted.

The skid plate 126 and the second instrument seal 128 have mounting holes 140 and 142, respectively. The mounting holes, 140 and 142, enable the skid plate 126 and the lower seal 128 to be mounted on a set of mounting pins 144 on the hinge plate 130. The second instrument seal 128 is sandwiched between the skid plate 126 and the cup-shaped first side 138 of the hinge plate 130. As illustrated, the second instrument seal 128 includes an annular flange 146, and is generally cup-shaped, see FIG. 5. The mating of the skid plate 126, seal 128 and hinge plate 130 provide a secure entrapment of the seal 128 to prevent movement as a small instrument is inserted.

Figure 5:
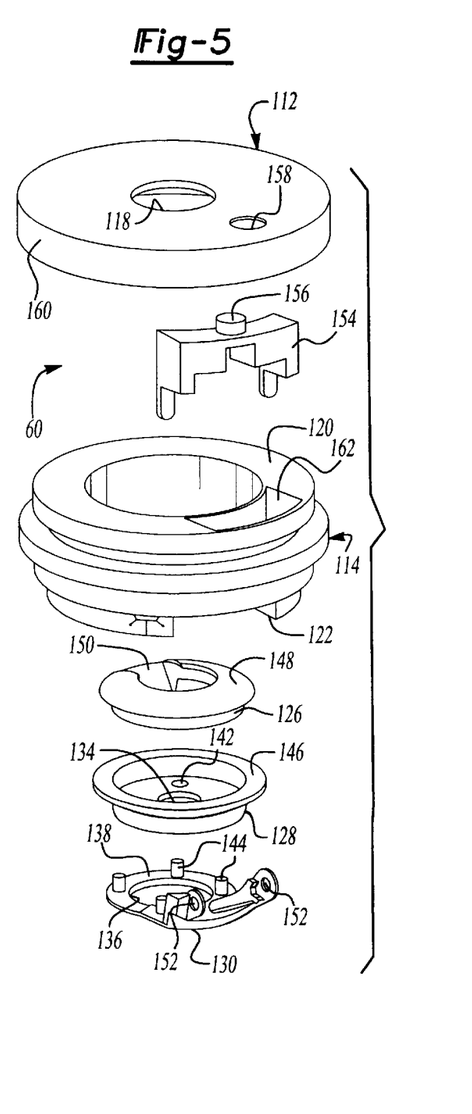
FIG. 5 is an exploded view of a portion of the interior of a trocar seal system designed according to this invention.

In FIG. 5, another orientation of an exploded view of a portion of the interior assembly 60 is shown. The dome-shaped surface 148 of the skid plate 126 includes a ramped portion 150. The ramped portion 150 and the dome-shaped surface 148 facilitate movement of the flapper door assembly 116 as a larger instrument is inserted and to guide a smaller instrument into the opening 134 in seal 128. This will be described in greater detail below. A pair of hinge pin holes 152 are located on the hinge plate 130. The hinge pin holes 152 receive the hinge pin 124 of the sleeve 114 to pivotally mount the hinge plate 130.

Figure 8:
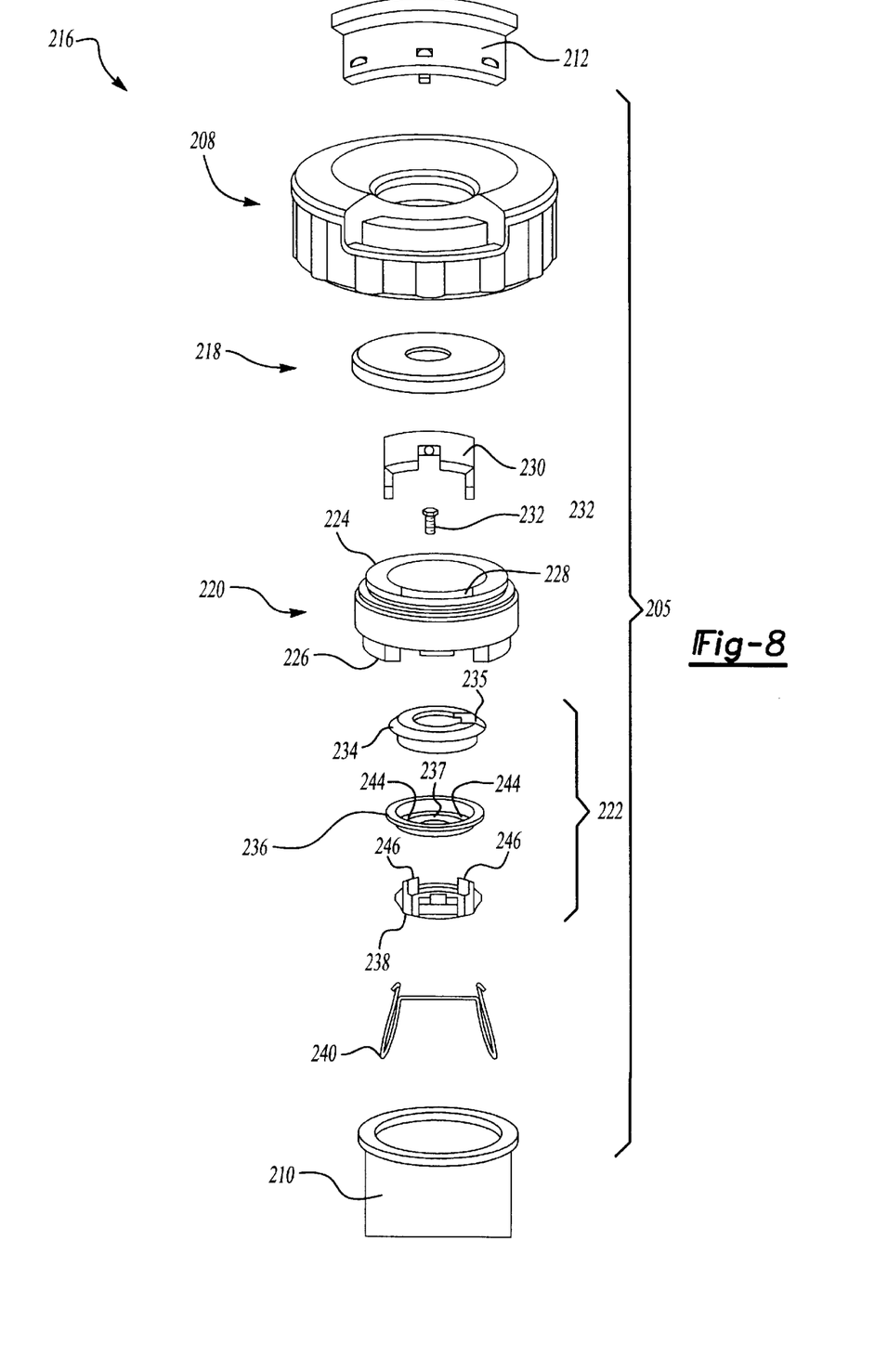
FIG. 8 is an exploded perspective view of the dual seal insert shown in FIG. 7 viewed from the top looking down.

The hinge plate 130 is biased by a spring 240 which is shown in FIG. 8, to a normally closed position against the second end 122 of the sleeve 114. Holes 132, 134 and 136 of the skid plate 126, second instrument seal 128, and hinge plate 130, respectively, are concentric. In one embodiment, the hole 118 of the first seal 112 is eccentric compared to the hole 134 of the second instrument seal 128. In another embodiment, the hole 118 of the first seal 112 is concentric compared to the hole 134 of the lower seal 128. The hole 118 of the first seal 112 is of a larger diameter than the hole 134 in the second seal 128. As illustrated, the first seal 112 is above seal 128, but it could be positioned below seal 128.

The interior assembly 60 includes a link 154 having a projection 156. The link 154 slidably fits under the seal 112 and within a release button slot 162 located in the first end 120 of the sleeve 114. The projection 156 extends into an opening 158 in the seal 112. The seal 112 has a lip 160 for mounting the seal 112 on the first end 120 of the sleeve 114.

Figure 6:
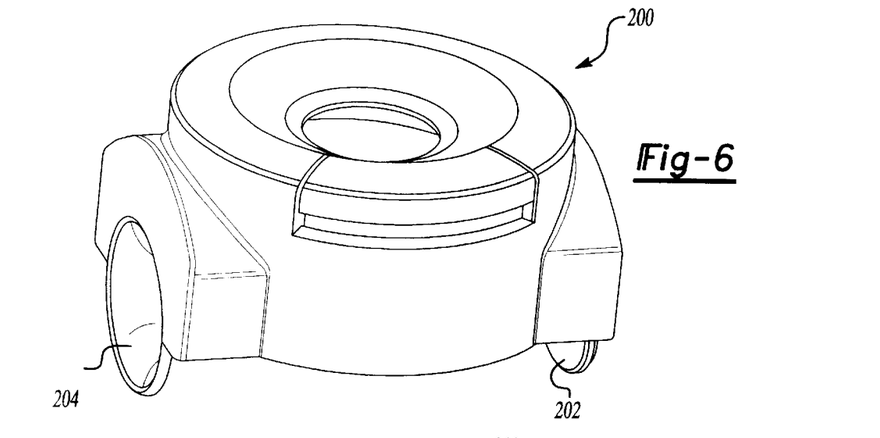
FIG. 6 is a perspective side view of an alternative trocar seal system designed according to this invention.
Figure 7:
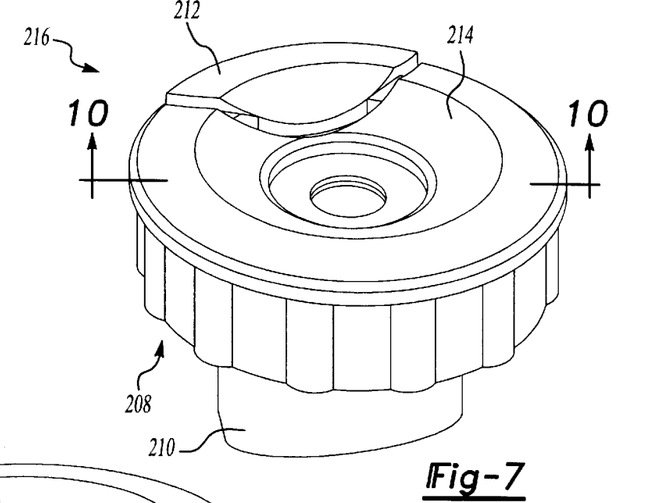
FIG. 7 is a perspective view of a dual seal insert designed according to this invention.

The link 154 is in contact with manual release button which is projection 156 in FIG. 6 or 212 in FIG. 7 and can be used by a surgeon to move the flapper door assembly to the open position to permit easier insertion of larger diameter surgical instruments or complex instruments.

In use, the trocar seal system 40 is inserted into the handle 24 of the cannula 14 and the first tabbed arm 50 and second tabbed arm 52 engage the notches 34 within the handle 24 of the cannula 14. The projecting lip 54 of the seal system 40 presses against the annular seal 30 of the cannula 14 and seals the trocar seal system 40 at the opening 28. The hole 118 of the upper seal 112 provides a means for maintaining the inflated state of the body cavity when surgical instruments having a diameter close to the diameter of the hole 118 are inserted through the cannula 14. When larger surgical instruments are inserted through hole 118, the leading end of the instrument strikes the ramped portion 150 of the skid plate 126 and moves the flapper door assembly 116 away from the second end 122 of the sleeve 114, bypassing holes 132, 134, and 136. This movement is facilitated by the ramped portion 150 and the dome-shaped surface 148. As stated above, the release button 154 provides a means for a surgeon to manually open the flapper door assembly 116, if desired.

When a surgical instrument of a smaller diameter is inserted through the hole 118 of the seal 112, the seal 112 does not provide a seal around the smaller diameter surgical instrument. But, because of the smaller diameter of the surgical instrument, when it approaches skid plate 126, the leading end of the instrument is directed through the holes 132, 134, and 136. Thus, the seal 128, through its hole 134, provides a seal around the smaller diameter surgical instrument. As will be understood by one of ordinary skill in the art, the skid plate 126 may have many alternative configurations. In particular, the surface 148 and the ramped portion 150 may have other configurations which still direct smaller instruments through the seal 128 and which permit larger instruments to move the flapper door assembly 116 into the open position.

In FIG. 6, a perspective side view of an alternative embodiment of a trocar seal system 200 is shown. The trocar seal system 200 includes tabbed arms 202 and 204. The tabbed arms 202 and 204 permit trocar seal system 200 to be releasably mounted onto the handle 24 of a cannula 14 in the same manner as trocar seal system 40, shown in FIG. 3. The internal elements of seal system 200 are the same as those found in seal system 40.

In FIGS. 7–10, a still further embodiment of a trocar seal system is shown generally at 216. The seal system 216 that is illustrated is adapted to thread onto a reusable trocar, however, it should be appreciated that it could be threaded onto a disposable trocar or configured to snap onto a trocar in the same manner as the previous two snap on seal systems described above. In addition, the seal system 216 could be integral with a trocar.

The seal system 216 includes a housing 208, s duckbill-type valve 210, and the interior seal assembly shown generally at 205 in FIG. 8.

In FIG. 8, an exploded perspective view of the dual seal assembly 216 is illustrated. The assembly 216 includes an upper seal 218, a sleeve 220 and a flapper door assembly 222. The sleeve 220 has a first end 224 and a second end 226. The upper seal 218 is adapted to fit over the first end 224.

The sleeve 220 includes a slot 228 that receives a link 230 and a compression spring 232. The compression spring 232 and the link 230 are maintained in the slot 228 by the upper seal 218 and the compression spring 232 biases the link 230 against the upper seal 218 and button 212.

The flapper door assembly 222 includes a skid plate 234 having a ramped portion 235, a lower seal 236, a hinge plate 238 having a hinge pin 239, and a spring 240. The skid plate 234, shown in FIG. 8, is similar in shape to skid plate 126 shown in FIG. 4. The lower seal 236 includes slots 244 that are received on posts 246 located on the hinge plate 238. The lower seal 236 includes a central opening 237 to permit surgical instruments to pass through the lower seal 236. The hinge pin 239 pivotally mounts the hinge plate 238 to the sleeve 220.

In this embodiment, the flapper door assembly 222 can be manually opened by depressing button 212. Button 212 operatively engages link 230 which is biased by spring 232. The link 230 and spring 232 are mounted within slot 228 in sleeve 220. The link 230 engages the flapper door assembly 222 when button 212 is depressed forcing the flapper door assembly 222 to the open position.

Figure 9:
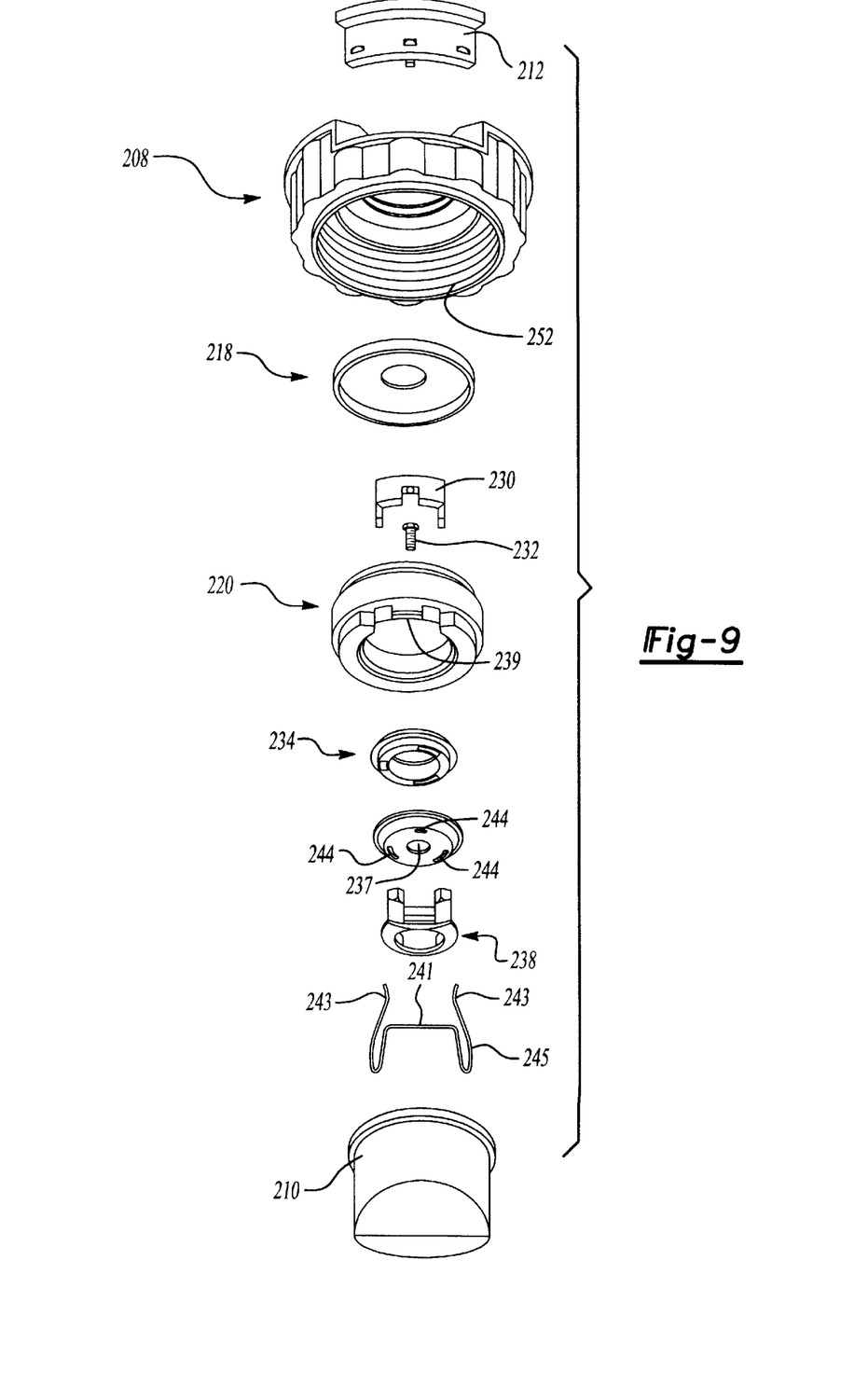
FIG. 9 is an exploded perspective view of the dual seal insert as shown in FIG. 7 viewed from the bottom looking up.

Housing 208 may include a set of internal threads 252 to permit it to be mounted into a reusable trocar (not shown), which is generally made of titanium, see FIG. 9.

Figure 10:
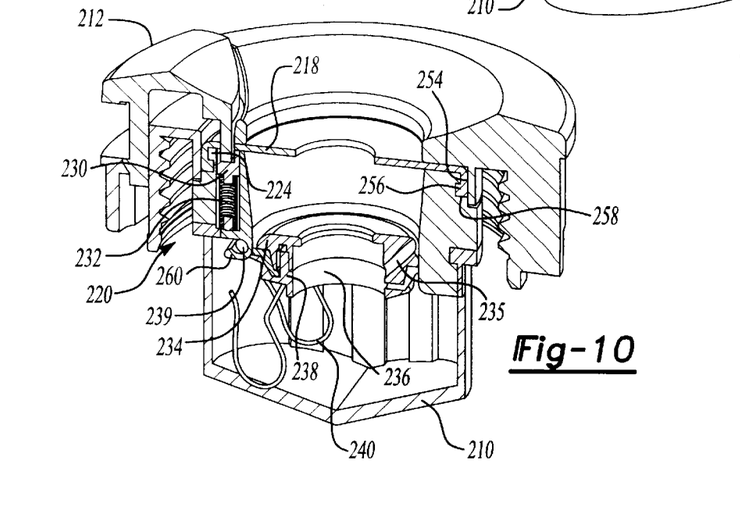
FIG. 10 is a cross-sectional perspective view of the dual seal insert along lines 10—10 of FIG. 7.

With reference to FIG. 10, the upper seal 218 includes a lip 254 having an inwardly extending flange 256. Lip 254 fits around first end 224 of sleeve 220 and flange 256 is received in a groove 258 located in sleeve 220. Hinge pin 239 is pivotally mounted in a pivot portion 260 of sleeve 220. Spring 240 is positioned between a lower portion 261 of duckbill valve 210 and hinge plate 238.

The shape of spring 240 and its orientation with respect to hinge plate 238 is specifically designed to provide a greater biasing force against pivoting of the hinge plate 238 when the hinge plate 238 is in the closed position (as shown in FIG. 10) and a reduced biasing force against pivoting of the hinge plate 238 as the hinge plate 238 is pivoted progressively away from sleeve 220. When a large diameter instrument is inserted through the converter 216, the upper seal 218 seals around the instrument. After further insertion, the large diameter instrument strikes hinge plate 238 and pivots it away from sleeve 220. The spring 240 provides a high initial bias, allowing less instrument drag and it decreases as the lower seal 236 is pivoted out of the way. When a small diameter instrument is inserted into seal 216 it engages lower seal 236. When the small instrument engages the lower seal 236, the initial high biasing force of spring 240 prevents hinge plate 238 from pivoting away from sleeve 220 and permits the lower seal 236 to seal around the smaller diameter instruments as it is inserted. The spring 240 has a crossbar 241 which engages the hinge plate 238 and spring legs 243 which are inserted into apertures (not shown) in sleeve 220. In the preferred embodiment, the sleeve 220 is ultrasonically sealed within housing 208.

The duckbill valve 210 maintains a seal when instruments are not present.

As will be appreciated by one of ordinary skill in the art, a duckbill valve normally remains closed due to the configuration of the valve.

Preferably, seals 112, 218, 128 and 236 are made of a silicone membrane having a hardness of between 20 and 50 durometer Shore A. In addition, it is preferable that these seals be coated with lubricating materials such as paralyne to reduce instrument drag against the seals.

Figure 11:
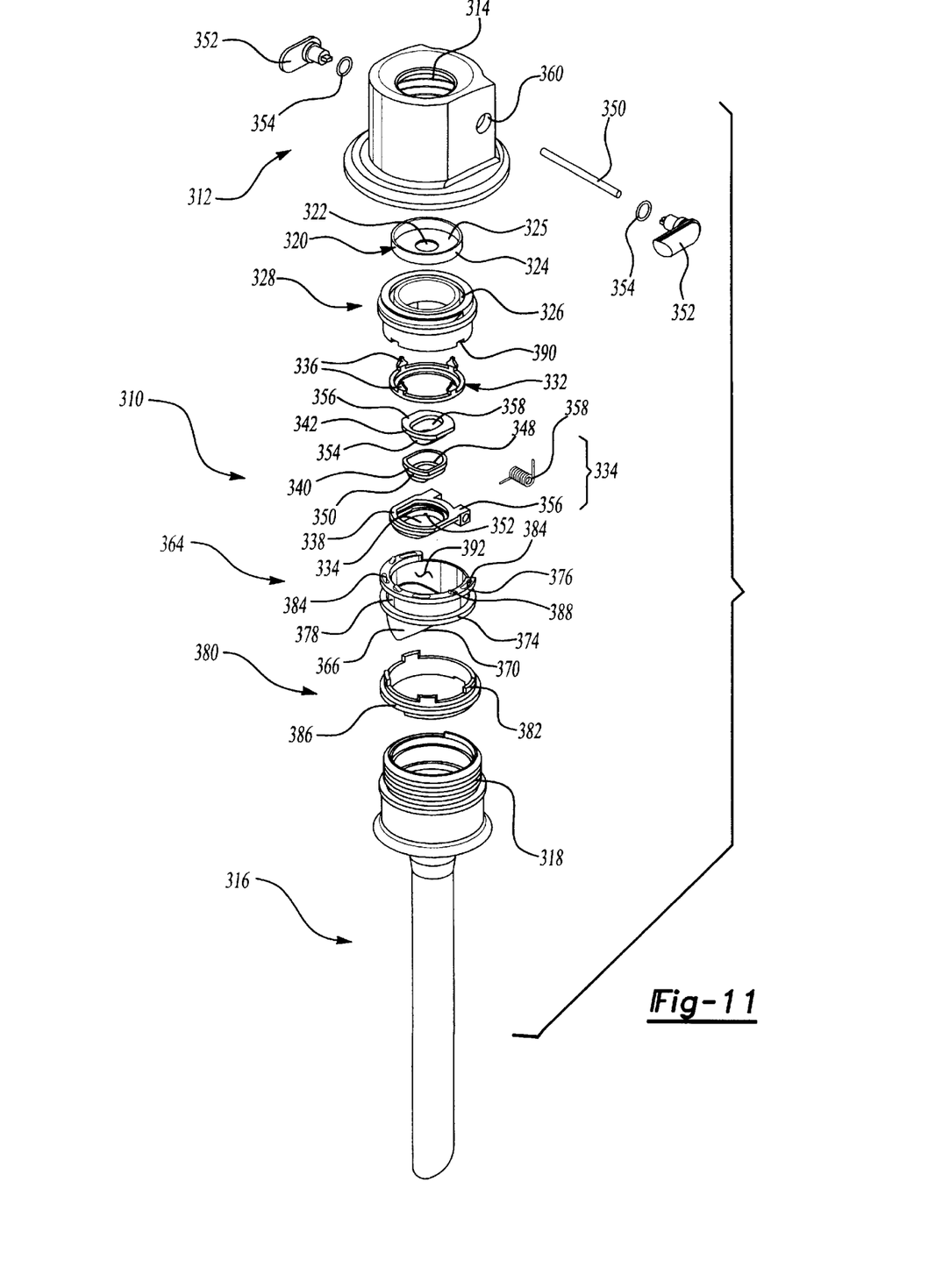
FIG. 11 is an exploded perspective view of a further embodiment of the dual seal assembly of the present invention looking from the top down.

With reference to FIG. 11, a further embodiment of the seal assembly of the present invention is generally shown at 310. Seal assembly 310 includes a housing 312 which has an internally threaded bore 314 for threaded attachment to the cannula 316 which has mating external threads 318. In use, the seal assembly is threaded onto the cannula 316 for sealing receipt of surgical instruments of various sizes.

Mounted in the housing 312 is first seal 320. First seal 320 has a hole 322 for sealing against medical instruments within a certain size range and preferably against larger instruments. The first seal 320 has a peripheral lip 324 that is mounted into a groove 326 in annular sleeve 328. As illustrated, the lip 324 extends above and below the face 325 of seal 320. The top of the lip seals against the inner top of the housing 312. It will be appreciated by those of ordinary skill in the art that the inner top housing 312 could have a groove to receive lip 324 which is preferred, or lip 324 could be squeezed against the inner top to provide a seal. The sleeve 328 has exterior threads 330 that mate with the interior threads of bore 314 so that sleeve 328 can be threaded into housing 312 for attachment.

Figure 12:
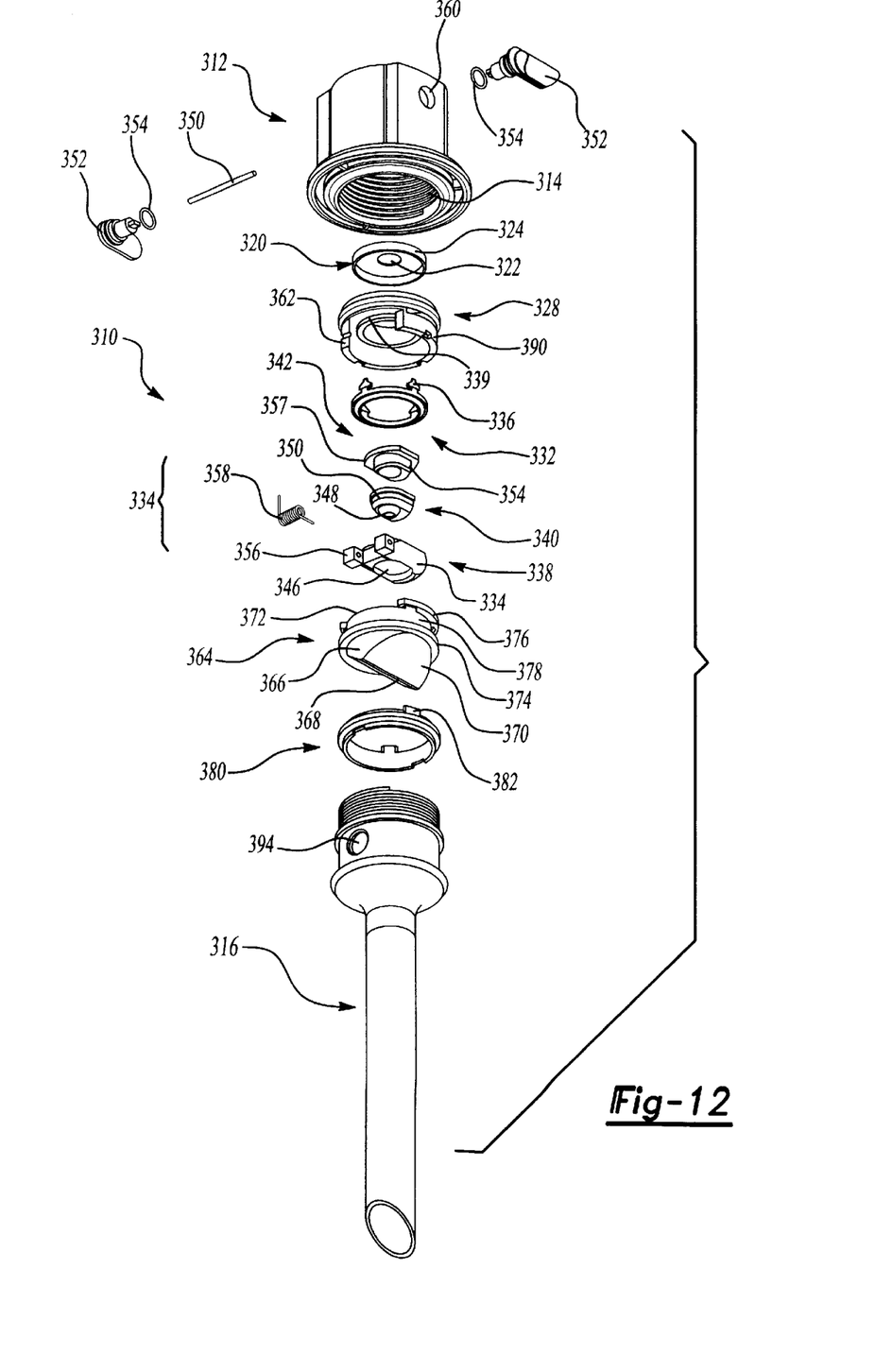
FIG. 12 is similar to FIG. 11 except it is a perspective view looking from the bottom toward the top.

A door seal 332 is mounted to the opposite side of the sleeve 328. The door seal 332 provides a sealing surface for the flapper door assembly 334. In the preferred embodiment, the door seal has tabs 336 that are received in slots 339 (see FIG. 12) which extend through the sleeve 328. In the preferred embodiment, the slots 339 extend from the bottom of the sleeve 328 into the groove 326. This reduces the required length of the tabs 336. The tabs are pushed through the slots 339 which compresses the tabs until the tabs exit the slots on the opposite side where they expand to hold the door seal in place.

The flapper door assembly is generally illustrated at 334. The flapper door assembly 334 includes the flapper door 339, second seal 340 and skid plate 342. The flapper door 339 has a pocket 344 which is open at the bottom at 346. The seal 340 is dome shaped to fit into the pocket 344. Seal 340 has an opening 348 which has a diameter for receipt of smaller surgical instruments. As illustrated, the seal 340 is stepped at 350 to mate with steps 352 in pocket 344. The mating steps provide added retention to the seal 340 in pocket 344.

The skid plate 342 is mounted into the recess of the dome shaped seal 340. The skid plate 342 has a base 354 and surface 356 that creates a flange 357 with respect to base 354. The top step 350 of seal 340 is a flange and it rests on top step 352 of pocket 344 and flange 357 fits into the flapper door 338 to sit on top of flange 357. In the preferred embodiment, the surface 356 is ultrasonically welded to the flapper door 338 to create the flapper door assembly 334. The skid plate has an opening 358 which is concentrically aligned with the openings 348 and 346 of the seal 340 and flapper door 338 respectively.

The flapper door assembly 334 is mounted to the housing 312 by a rod 350, levers 352 and 0-rings 354. The rod 350 is received by mounting ears 356 formed in flapper door 338. A coil spring 358 provides a bias to normally close the flapper door assembly 334. The rod extends through opening 360 in the housing to mount the flapper door assembly to the housing 312. The coil spring 358 has its free ends mounted in apertures in the flapper door 338 and in the sleeve 328. In the disclosed embodiment, the sleeve 328 is recessed at 362 to receive the ears 356 of the flapper door assembly 334. Additionally, the duckbill valve 364 is recessed 372 to provide clearance to the flapper door assembly 334.

Duckbill valve 364 is mounted in the housing 312. The valve 364 provides sealing when no instrument has been inserted. The base 366 of the valve 364 is angled at 370 and ends in a slit 368 that is normally closed. The angled walls 370 are forced by pressure within the cannula 316 to the closed position. The upper portion of the valve 362 has two spaced flanges 374 and 376 to define a recess 378. A retainer ring 380 fits about the recess 378 between the flanges 374 and 376. The retainer ring 380 has tabs 382 which are received in slots 384 to lock the duckbill valve 364 to the ring 380. The exterior of the ring 380 has threads 386 and they mate with the internal threads in bore 314. The top of flange 376 has small tips 388 that are received in notches 390 of sleeve 328 to provide rotational alignment between the duckbill valve 380 and the housing 312. The duckbill valve 380 has an opening 392 for receipt of an instrument that is inserted through the housing 312.

In this embodiment, the cannula illustrated has an inlet opening 394 for receipt of a valve to allow the introduction of gas into a body cavity. The valve is not shown.

As with the previous devices described, the seals 320, 332, 340 and 364 are preferably made of a silicone material having a hardness of between 20 and 50 durometer Shore A. Further, seals 322, 340 and 364 are coated with a lubricating material such as paralyne. The housing 312, sleeve 328, flapper door 338, skid plate 342, and ring 380 are preferably made of plastic.

The seal assembly 310 of this embodiment is used in the same manner as previous dual seal assemblies. The dual seal assembly is threaded onto the cannula 316 of this embodiment. It should be understood that it could include other types of attachment devices. Once it is secured on the cannula 316, instruments of various sizes can be inserted through the seal and into cannula 316 without losing the gas pressure in the body cavity. When no instrument is inserted, the duckbill valve 364 remains closed and maintains gas within the body cavity. Upon insertion of a larger diameter instrument, the seal 320 seals against the instrument as the instrument is inserted. As the instrument reaches the flapper door assembly 334, its larger size will cause the instrument to engage the skid plate 342, pivoting the flapper door assembly 334 out of the path of the instrument so that the instrument can pass through the duckbill valve 364 and through cannula 316. As in previous embodiments, the skid plate 342 has an angled surfaced 358 which facilitates the movement of the flapper door assembly out of the path of the larger diameter instruments. With larger diameter instruments, the seal 320 provides the sole sealing against the release of pressure.

When smaller diameter instruments are inserted into the dual seal assembly 310, they pass freely through the opening 322 in seal 320 without being sealed. As the instrument is further inserted, it engages the skid plate 342 and is directed by incline surface 358 into the opening in the skid plate and through the opening 348 in seal 350. Coil spring 358 maintains the flapper door in the path of the instrument so that the instrument is forced to slide through opening 348 in seal 350 then pass through the duckbill valve 364 into cannula 316.

It should be appreciated by the those of ordinary skill in the art that the use of the dual seals reduces the drag upon instruments that have been found in other types of sealing arrangements which try to expand for various diameter tools. In this embodiment, full and complete sealing is obtained for various diameter instruments without any undue drag being felt by the user of the and dual seal assembly of the present invention. Furthermore, sealing is automatic. One of ordinary skill in the art will also appreciate that although the illustrations show the flapper door assembly below the seal for larger instruments, the flapper door assembly could be above the other seal.

The foregoing description is exemplary rather than limiting in nature. Variations and modifications to the disclosed embodiment may become apparent to those skilled in the art and do come within the scope of this invention.

What is claimed is:

1. A cannula seal comprising:

a housing having an instrument path, said housing for connecting to a cannula;

a first seal mounted in said housing, said first seal having an opening to sealingly receive an instrument having a first diameter; a second seal mounted in said housing, said second seal having an opening to sealingly receive an instrument having a second diameter;

said second seal being pivotally mounted within said housing and being adapted to pivot out of said instrument path to allow an instrument having a diameter greater than the opening in said second seal to pass by said second seal; said second seal is mounted with a sub-assembly which is hinged to said housing by a hinge said sub-assembly includes a door having a pocket to receive said second seal and a skid plate mounted to said door over said second seal to hold said second seal between said skid plate and said door retaining said second seal within said sub-assembly.

2. The trocar seal of claim 1 wherein said skid plate has an angled aperture which is angled in the direction of said hinge.

* * * * *